United States Patent
Abraham et al.

(10) Patent No.: US 9,173,560 B2
(45) Date of Patent: Nov. 3, 2015

(54) METHOD FOR DETERMINING DEVIATIONS BETWEEN COORDINATE SYSTEMS OF DIFFERENT TECHNICAL SYSTEMS

(75) Inventors: Mario Abraham, Burgthann (DE); Johannes Agethen, Erlangen (DE); Mario Klafke, Mainaschaft (DE); Joachim Matschnigg, Nürnberg (DE)

(73) Assignee: Wavelight GmbH (DE)

( * ) Notice: Subject to any disclaimer, the term of this patent is extended or adjusted under 35 U.S.C. 154(b) by 561 days.

(21) Appl. No.: 13/577,385

(22) PCT Filed: Feb. 15, 2010

(86) PCT No.: PCT/EP2010/000920
§ 371 (c)(1),
(2), (4) Date: Aug. 6, 2012

(87) PCT Pub. No.: WO2011/098098
PCT Pub. Date: Aug. 18, 2011

(65) Prior Publication Data
US 2012/0307207 A1    Dec. 6, 2012

(51) Int. Cl.
*A61B 3/14* (2006.01)
*A61B 3/113* (2006.01)
*A61F 9/008* (2006.01)

(52) U.S. Cl.
CPC .......... *A61B 3/113* (2013.01); *A61F 9/00802* (2013.01); *A61F 2009/00846* (2013.01); *A61F 2009/00872* (2013.01)

(58) Field of Classification Search
CPC ....... A61B 3/1025; A61B 3/103; A61B 3/113
USPC .................. 351/204, 205, 209, 210, 212, 246
See application file for complete search history.

(56) References Cited

U.S. PATENT DOCUMENTS

| 4,134,681 A | 1/1979 | Elmer |
| 2002/0082590 A1* | 6/2002 | Potgieter .......................... 606/4 |

(Continued)

FOREIGN PATENT DOCUMENTS

| WO | 01/44962 A1 | 6/2001 |
| WO | 02/056789 A2 | 7/2002 |

(Continued)

OTHER PUBLICATIONS

A.S. Nazarov; "The Transformation of Coordinate Systems"; Minsk; 2008; pp. 62-70.

(Continued)

*Primary Examiner* — Huy K Mai (57) ABSTRACT

Method for determining deviations between coordinate systems of different technical systems, comprising the steps of determining a coordinate position of a reference feature of a test object in the coordinate system (u,v) of a first of the technical systems, the attachment of at least one test feature to the test object, with the test feature being attached in the coordinate system of a second of the technical systems at a coordinate position that is determined in dependence on the determined coordinate position of the reference feature, the determination of a coordinate position of at least one test feature and/or at least one feature derived from it in the coordinate system (u,v) of the first technical system, and determination of deviations between the coordinate systems of the first and second technical system, at least on the basis of: (a) the determined coordinate position of at least one test feature and/or of at least one feature derived from it in the coordinate system (u,v) of the first technical system and (b) the coordinate position of the reference feature in the coordinate system (u,v) of the first technical system.

19 Claims, 2 Drawing Sheets

(56) References Cited

U.S. PATENT DOCUMENTS

2003/0223037 A1   12/2003   Chernyak
2005/0024586 A1    2/2005   Teiwes et al.

FOREIGN PATENT DOCUMENTS

WO     02/064031 A2    8/2002
WO  2007/027562 A1    3/2007

OTHER PUBLICATIONS

Yang, HongXing, "The Research on Calibrating In Vision-Guide Motion Control System", Proc. of SPIE, Jul. 10, 2009, pp. 748908-1-748908-4, vol. 7489, PIAGENG 2009.

\* cited by examiner

METHOD FOR DETERMINING DEVIATIONS BETWEEN COORDINATE SYSTEMS OF DIFFERENT TECHNICAL SYSTEMS

This is a United States national phase application of co-pending international application number PCT/EP2010/000920 filed on Feb. 15, 2010, the disclosure of which is incorporated herein by reference.

TECHNICAL FIELD

The invention relates to a method for determining deviations between coordinate systems of different technical systems.

BACKGROUND

Technical systems often operate with coordinate systems which they require for determining the position of occurring events, of actions to be carried out and/or of objects in motion or at rest. Sensor systems that detect the location of an event or of an object in a single- or multi-dimensional coordinate system, are examples of this. Such sensor systems can, for example, be camera-based and be configured as a motion tracking system. Such motion tracking systems are used to recognize and track the (changeable) position of moving objects.

One example of a motion tracking system especially considered within the framework of the invention is a so-called eye tracker, by which eye movements can be detected. Use of eye trackers is current practice in laser-surgery ophthalmology, thus processing of the human eye by means of laser radiation for the purpose of eliminating or at least reducing incorrect functions or pathology of the eye.

Without mechanical fixing, the human eye never is totally still, but rather even when taking aim at a specific fixation target it continues to make smaller and larger movements (such as the saccades), and therefore with various techniques of eye treatment by laser surgery, an eye tracker is used, to detect movements of the eye to be treated, and depending on the detected eye position, to guide the treating laser. As an example in this regard, especially refractive laser treatment is especially named, in which corneal tissue is ablated (i.e. removed from the surface) using laser radiation in the UV wavelength range, in this way to reform the corneal front surface and by this means to alter the refractive properties of the cornea. One example of such a refractive technique is so-called LASIK (Laser In Situ Keratomileusis), in which at first by means of a mechanical microkeratom or by means of femtosecond laser radiation, laser radiation cuts out from the cornea a small covering disk customarily designated in the technical world as a flap. The flap is not totally separated from the corner, but still hangs in a hinge area on the remaining corneal tissue. The flap is then pivoted to the side and the corneal material thus revealed is subjected to an ablating laser treatment. Then the flap is pivoted back again. Because the outer epithelium layer of the cornea is only slightly damaged in this method, the wound heals relatively quickly.

Laser devices that generate a positionally controllable laser beam for processing a material, are another example of technical systems that operate with a coordinate system. The ablation positions of the laser beam, thus those positions to which the laser beam is to be directed, can be defined by coordinate positions in the coordination system of the laser device. With laser devices that generate pulsed laser radiation, every coordinate position can be assigned to a single laser pulse or a group of laser pulses.

SUMMARY OF EXAMPLE EMBODIMENTS

The above reference to using an eye tracker in laser surgery treatment of the human eye makes it already clear that in practice solutions often occur in which multiple technical systems, each with its own coordinate system, operate together. If one of the technical systems transmits coordinate values that it determined or fixed with reference to its own coordinate system, to another technical system, that receives these transmitted coordinate values to determine the coordinate positions of an action to be taken in its coordinate system, for example, problems can arise if the coordinate systems of the two technical systems are not mutually adjusted. It is readily imagined that a certain point in a space in a coordinate system of the one technical system can have coordinate values different from the same space point in the coordinate system of the other technical system. This can for example be at a different place of the coordinate center of the two coordinate systems in space. The two coordinate systems can also be distorted relative to each other. Another cause can be in an a different scaling of the coordinate axes, i.e., the same nominal coordinate values along an axis can be at a different distance from the coordinate origin from that in the other coordinate system.

If the coordinate systems of different technical systems operating in concert with each other are not spatially identical to each other, for proper functioning of the cooperation at minimum it is necessary to have precise knowledge about the differing spatial position and/or the differing scaling of the coordinate systems, to be able to convert a coordinate position from one of the coordinate systems into a corresponding coordinate position of another coordinate system. Often this knowledge is not present and must be laboriously determined.

U.S. Pat. No. 4,134,681 is concerned with determining the relative orientation of two physical systems. For two beam vectors that for example indicate the direction of a laser beam, the particular vector direction is determined in the coordinate systems of the two physical systems, so that altogether four directional vectors are obtained, two for each coordinate system. From these four directional vectors, then the relative orientation of the two coordinate systems, and thus of the two physical systems, is determined.

The task of the invention is to indicate a simple method, and, above all, one that is accessible to automated implementation, for determining deviations between coordinate systems of different technical systems.

To solve this problem, in agreement with the features of claim 1, the invention provides a method for determining the deviations between coordinate systems of different technical systems, comprising:

determination of a coordinate position of a reference feature of a test object in the coordinate system of a first of the technical systems, attachment of at least one test feature to the test object, with the test feature being attached in the coordinate system of a second of the technical systems at a coordinate position that is determined in dependence on the determined coordinate position of the reference feature, determination of a coordinate position of at least one test feature and/or at least one feature derived from it in the coordinate system of the first technical system, and determination of deviations between the coordinate systems of the first and second technical system, at least on the basis of:

(a) the determined coordinate position of at least one test feature and/or of at least one feature derived from it in the coordinate system of the first technical system, and (b) the coordinate position of the reference feature in the coordinate system of the first technical system.

With the invention-specific solution, in one embodiment a test object is used that is provided with a reference pattern which can be detected by a first of the technical systems. The reference pattern can directly form the reference feature. Alternatively, the reference pattern can be configured so that a reference feature can clearly be derived from it. For example, the reference feature can be the center (midpoint) of a geometric object serving as the reference pattern. Algorithms which compute the midpoint from a detected geometric form are known per se and do not need to be explained in detail here. In any case, in a preferred embodiment, the first technical system is in a position, based on the detected reference pattern, to determine the coordinate position of the reference feature in its coordinate system (i.e., in the coordinate system of the first technical system).

The coordinate position thus determined (depicted by one or more coordinate values) is then transmitted by the first technical system to a second of the technical systems. The second technical system uses the transmitted coordinate values of the reference feature as if they were coordinate values of its own coordinate system (i.e., of the coordinate system of the second technical system), and in its coordinate system determines the coordinate position for a test feature to be generated in accordance with a preset generation rule depending on the transmitted coordinate position of the reference feature. For example, for the test feature, a generation rule can be preset that along at least one part of the coordinate axes of the coordinate system of the second technical system it has a preset coordinate distance from the reference feature. Through such a generation rule, in the coordinate system of the second technical system, the position of the test feature can clearly be set with reference to the position of the reference feature.

In a preferred embodiment, the second technical system then attaches a coordinate position determined in the above manner, dependent on the coordinate position of the reference feature, to the test feature. If multiple test features are to be attached, the second technical system acts in a corresponding manner for each of the test features.

In a following step, the test object with the reference pattern and the attached test features is again investigated by the first technical system. The first technical system determines which coordinate position at least one test feature and/or a feature derived from it has in the coordinate system of the first technical system. Based on this, now one or more deviations can be determined within the coordinate system of the first technical system. Preferably at least one displacement vector is determined, by which the coordinate system of the second technical system is spatially displaced vis-à-vis the coordinate system of the first technical system, and/or a relative twisting is determined between the coordinate systems of the two technical systems and/or scaling differences are determined between the coordinate systems of the two technical systems.

The deviations determined can be converted into one or more correction factors that are consulted by the second technical system in later operations for correction of any coordinate positions that it receives as transmitted from the first technical system. In this way, successful adjustment is made in the coordinate systems of the two technical systems.

In one preferred embodiment, as part of the invention-specific method, multiple test features are attached to different locations of the test object. At least one part of the test features can be attached in a polygon arrangement, for example a rectangular arrangement, round about the reference feature on the test object. Then as a derived feature, a polygonal center of the test features arranged as a polygon can be determined, and in the coordinate system of the first technical system a deviation can be determined between the coordinate position of the reference feature and the coordinate position of the polygon center.

According to another embodiment, the deviations between the coordinate systems of the first and second technical systems are further determined on the basis of a target coordinate position of at least one feature among the testing and derived features in the coordinate system of the first technical system. The target coordinate position of a test feature can be determined, for example, by application of the previously-mentioned generation rule in the coordinate system of the first technical system. If for example the generation rule for the test feature makes provision for a preset x-distance and a preset y-distance of the reference feature along two axes x, y of the coordinate system of the second technical system, then the target coordinate position of the text feature in the coordinate system of the first technical system can be determined by these same nominal (numerical) coordinate distances being applied to the determined coordinate position of the reference feature.

According to a preferred embodiment form, the first technical system comprises a motion tracking device with a camera directed at the test object, with the motion tracking device determining the coordinate position of the reference feature and of at least one testing and/or derived feature in a first coordinate system.

The test object can bear a pattern, the center of which is determined by the motion tracking device as the reference feature. The pattern (reference pattern) can for example be a flat pattern that is optically contrasted vis-à-vis the surrounding area. Optical contrast should exist at least at the boundary of the reference pattern with the surrounding area. It can be brought about at least in part by differing gray stages or differing color tones of the pattern and of the surrounding area. Alternatively or additionally, it is possible to generate or amplify the contrast between the reference pattern and the surrounding area, by having the two areas obtain differing surface treatments, or one of the areas obtaining a surface treatment while the other area remains without it. For example, the surrounding area of the reference pattern can be provided with a network of printed points or lines, while the reference pattern remains patternless and is covered over its entire surface by a specific gray or color tone.

In other respects it is not necessary that the reference pattern and/or the surrounding area have only a single color. A color or gray-stage gradation can be implemented within the reference pattern and/or within the surrounding area.

The reference pattern can have a round outline, for example a circular or elliptical outline. In this way a two-dimensional projection of a human pupil can be simulated. The size of the reference pattern can at least approximately correspond to a human pupil. In this case, the reference pattern represents a pupil model. This is appropriate in that image processing algorithms that compute the position of a pupil center from a pictorially detected pupil of the eye, are known per se and can be obtained on the market. A test object with such a pupil model is especially suited therefore for application of the invention as part of a device for laser surgery treatment of the human eye. It is readily understood that non-round outline shapes of the reference pattern are equally possible, as long as it is ensured that the reference pattern possesses a clearly determinable center. Also, the reference pattern does not have to correspond in size to a human pupil. It can be larger or smaller.

The second technical system preferably comprises a laser device which applies at least one test feature by means of a laser beam, especially a pulsed laser beam, to the test object. The laser device uses a second coordinate system for positioning of the laser beam.

To be able to do good detection with an eye tracker or generally with a camera-based motion tracking device of the attached test feature, it is recommended that for attachment of a test feature, the test object be treated with a laser beam so that there arises a local coloring and/or local cratering of the test object.

The at least one deviation determined is appropriately used for correction of coordinate data, which the second technical system receives as transmitted from the first technical system and which it needs for its operation. The at least one deviation determined can be converted into one or more suitable correction or calibration factures, which are applied to the coordinate data transmitted from the first technical system.

The invention further relates to a test object for use in a method of the type mentioned above. The test object possesses a pattern that stands out optically (reference pattern) and at least in one area around the pattern is configured so that through local laser irradiation, test features that stand out optically can be generated.

Preferably the pattern is an areal pattern which can model a human pupil and appears in a first color, while the test object appears in an area around the pattern in a second color. The second color is different from the first color. The term "color" here is to be broadly understood. Different colors can for example be implemented by different color tones (including gray) or by different gray stages or by differing brightness values of a color tone.

According to one example, the first color can be printed on a substrate of the test object. In the area surrounding the reference pattern, the substrate can have a single colored layer with a color differing from the first color. By laser irradiation this colored layer (white, for example) can then undergo color alteration, thus allowing the test features to be perceptible. But it is also possible for the substrate in the surrounding area to have multiple differing color layers one above the other, of which the uppermost (outermost) displays the second color, so that the test object appears in the surrounding area in the second color. With laser irradiation, the second color can be bleached out or disappear by some other means, through which the color layer lying underneath can be revealed. On the one hand this ensures that the reference pattern is easily recognized, and on the other hand, at least one test pattern is easily recognized.

For example the test object is configured as a plate or sheet. It can display a piece of paper or cardboard, for example, which bears the pattern on its flat sides and is simultaneously configured there for generation of the test features. The piece of paper or cardboard can for example be glued to a stable carrier plate made of metal or plastic, to make the test object overall sufficiently stiff and robust.

In one variation, the test object can possess a curved (or generally three-dimensional) surface, onto which the reference pattern is attached and the test features can be attached. For example, this surface can model the front surface of a human eye. It then can be necessary for adjustment of the coordinate systems to additionally make allowance for the curvature or curvature progression of the test object surface, to avoid any scaling errors.

Lastly the invention relates to a device for laser-surgery ophthalmology, comprising:
- a laser device to make available a pulsed focused laser beam and to direct same toward an eye to be treated,
- an eye tracker for detecting eye movements, and
- a control unit coupled with the eye tracker, which is furnished to control the laser device in dependence on the detected eye movement, wherein the control unit is additionally furnished for:
  (i) carrying out a method of the type mentioned above, to determine deviations between a first coordinate system used by the eye tracker and a second coordinate system used by the laser device, and
  (ii) to allow for determined deviations with the control of the laser device.

BRIEF DESCRIPTION OF THE DRAWINGS

In what follows, the invention will be further explained using the appended drawings. Shown are.

DETAILED DESCRIPTION OF THE DRAWINGS

Figure 1:
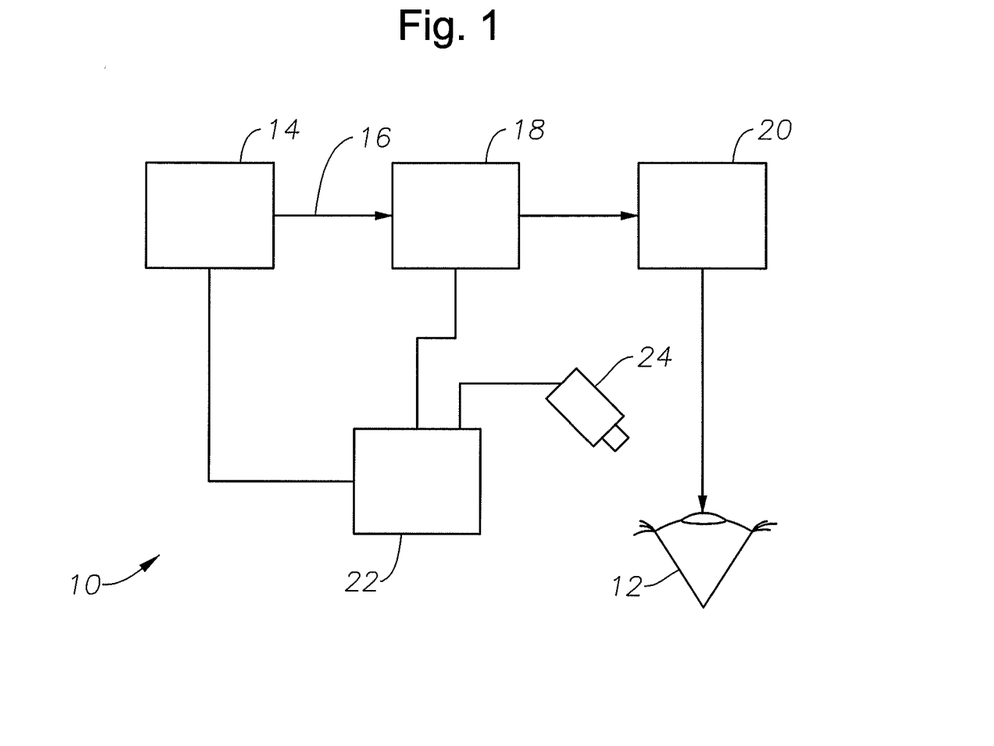
FIG. 1—an embodiment in a schematic block diagram of a device for laser-surgery ophthalmology FIG. 2—an example of spatial positions that differ from each other of two coordinate systems used in the device from FIG. 1

The device shown in FIG. 1, generally designated by 10 for laser-surgery ophthalmology, is set up to carry out corneal ablations of an eye 12 to be treated. It comprises a laser source 14 which generates a pulsed laser beam 16, that by means of a controllable deflection unit (scanner) 18 is specifically deflectable in a plane normal to the beam direction, hereinafter named the x-y plane. Placed next to the scanner 18 is a focusing unit 20, which focuses the laser beam 16 on the eye 12 to be treated.

For ablative treatments, the wavelength of the output of laser source 14 is in the ultraviolet range. For example, laser source 14 comprises an excimer laser emitting at 193 nm.

The scanner 18 is formed for example in a manner known per se by a pair of galvanometrically controllable deflection mirrors. The focusing unit 20 can be formed by a single lens or by a multi-lens system.

An electronic control unit 22 controls the laser source 14 and the scanner 18 in accordance with an ablation profile implemented by a control program, determined in advance for the patient. The ablation profile indicates how much corneal material must be removed at what location of the eye to be treated. Each laser pulse (shot) causes a specific amount of material to be removed. The control program causes as many laser pulses to be placed at each location in the ablation area as are needed to remove the desired material thickness. The ablation positions are depicted by pairs of coordinates that relate to the two axes of a (rectangular) x-y coordinate system that sets the mentioned x-y plane. The pairs of coordinates indicate the coordinate distance from a center of the ablation profile (ablation center) that typically is defined in dependence on the pupil center of the eye 12 to be treated. Unavoidable movements of the eye 12 lead to continual changes in the position of the pupil center, and consequently of the ablation center in the x-y coordinate system.

For monitoring eye movements, the device 10 comprises an eye tracking device 24 designated for short as an eye tracker, which with a camera, for example, takes an infrared image of the eye 12 and especially the iris with the pupil, and by means of suitable image-processing software computes the position of the pupil center. However, the eye tracker 24 does not operate with the same x-y coordinate system that the control unit 22 and the scanner 18 operate with. Rather, it computes the position of the pupil center in its own (rectangular) coordinate system, which for purposes of illustration is designated as a u-v coordinate system. In this u-v coordinate system, the eye tracker 24 indicates the position of the pupil center in like manner through a pair of coordinates, thus a coordinate value for the u-axis and the v-axis.

The control unit 22 obtains from the eye tracker 24 the u-v coordinate position of the pupil center and converts it into the corresponding x-y coordinate position. With this it relies back to initially determined correction information that represents any spatial position deviations and any scaling deviations between the two coordinate systems. The correction information can for example be implemented in the form of a correction function or in the form of one or more correction factor to be used multiplicatively or additively. From the position of the pupil center converted into x-y coordinates, the control unit 22 can then compute the current position of the ablation center and appropriately guide the scanner.

Figure 2:
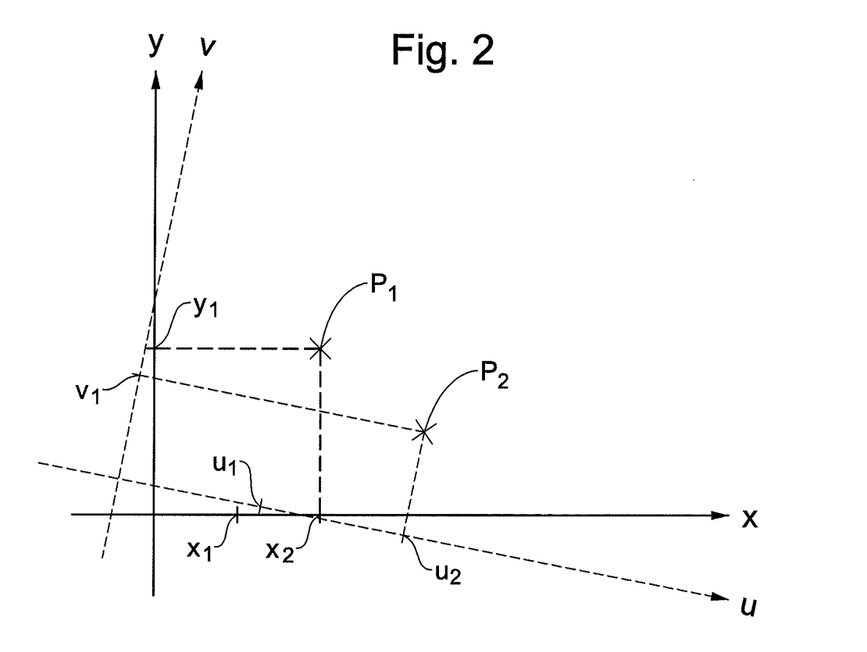

Shown schematically in FIG. 2 are possible deviations between the x-y coordinate system used by control unit 22 and scanner 18 and the u-v coordinate system used by eye tracker 24. To better distinguish, the x-y coordinate system is shown by continuous lines, while the u-v coordinate system is shown by dashed lines.

As a first deviation of the two coordinate systems in space, in the example case of FIG. 2, a different position of the coordinate origins is perceived, thus the crossing points of the coordinate axes. This differing spatial position can be expressed by a displacement vector.

As a second deviation, in the example case of FIG. 2, a relative twisting of the two coordinate systems is perceived. The measure of this twisting can be indicated by an angular value.

A third deviation of the coordinate systems can consist in a different scaling. To illustrate this situation, in FIG. 2 two coordinate values $x_1$, $x_2$ are identified on the x axis, which nominally correspond to two coordinate values $u_1$, $u_2$ drawn in on the u axis. Nominal correspondence means that the coordinate values $x_1$ and $u_1$ are numerically equal and the coordinate values $x_2$ and $u_2$ are also numerically equal.

True, it is easy to perceive that the coordinate value $x_1$ is at a considerably shorter distance from the center of the x-y coordinate system than the coordinate value $u_1$ is from the center of the u-v coordinate system. In the same way, the distance of the coordinate value $x_2$ from the center of the x-y coordinate system is smaller than the distance the coordinate value $u_2$ has from the center of the u-v coordinate system. If the numerical values of $x_1$ and $u_1$ agree and if the numerical values of $x_2$ and $u_2$ agree, this means that the scaling of the x axis is different from the scaling of the u axis.

In a similar way, in FIG. 2 on the y axis a coordinate value $y_1$ is drawn in, which in regard to its numerical value corresponds to coordinate value $v_1$ drawn on the v axis. True, here also the distances of the coordinate values $v_1$ from the center of the particular coordinate system are different. Namely, the distance of coordinate value $y_1$ from the center of the x-y coordinate system is considerably greater than the distance of coordinate value $v_1$ from the center of the u-v coordinate system. This also means a different scaling of the y axis in comparison to the scaling of the v axis.

Such scaling deviations can exist for all the axes of the coordinate systems, or for only a part of the axes.

Each of the explained three possible deviations results in points that are described in the x-y coordinate system and in the u-v coordinate system by these same coordinate values, having differing locations. This is illustrated in FIG. 2 by two example points $P_1$ and $P_2$. Point $P_1$ is defined by the coordinate values $x_2$, $y_1$, while point $P_2$ is defined by the coordinate values $u_2$, $v_1$. Despite the same numerical values for $x_2$ and $u_2$ as well as for $y_1$ and $v_1$, a distinct positional interval results for points $P_1$, $P_2$. But without the deviations mentioned (center shift, twisting, scaling difference), points $P_1$, $P_2$ would coincide.

Figure 3:
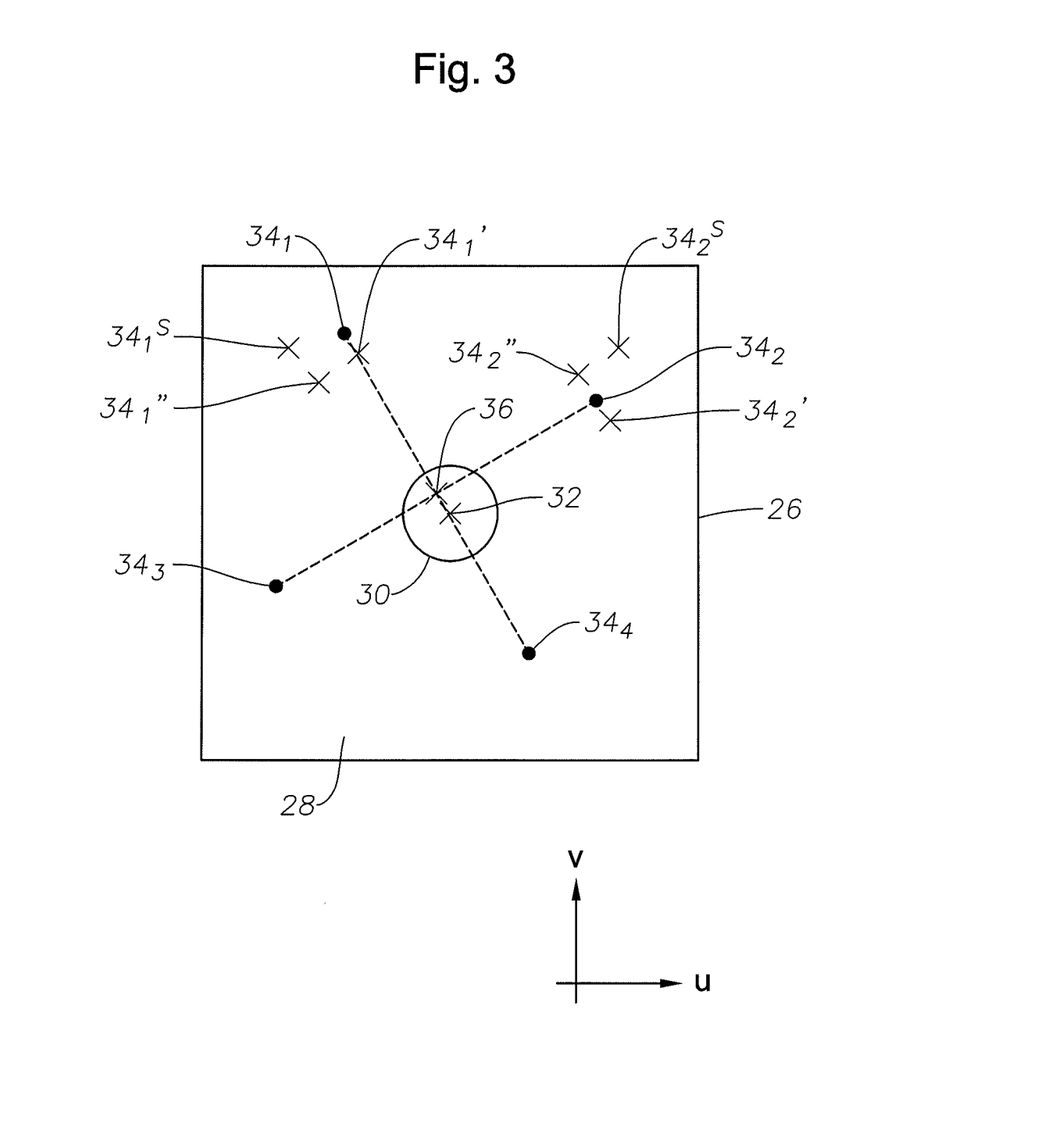
FIG. 3—an embodiment example of a test object usable for calibration of the device in FIG. 1.

FIG. 3 explains an embodiment example of a method to determine deviations between two coordinate systems of different technical systems. In the specific example case, reference is made to coordinate systems used by control unit 22 and scanner 18 on the one hand and eye tracker 24 on the other hand.

First, the eye tracker 24 investigates a test object 26, which is appropriately placed essentially at that position in device 10 at which the eye 12 to be treated later is located. Especially the test object 26 is so placed that it is in the focal plane of laser beam 16.

In the example shown, test object 26 has a flat top side 28, which roughly in the middle has a reference pattern 30 that stands out optically from the surrounding area. Reference pattern 30 is modeled as a pupil and correspondingly is formed by an approximately pupil-sized circular pattern preferably filled with color. The circular pattern 30 does not of necessity have to be exactly circular; it can also have more or less pronounced deviations from the circular form.

The image processing software incorporated in eye tracker 24 recognizes the pupil pattern 30 and from it computes the position of the center of the pattern in its u-v coordinate system. The center of the pattern in FIG. 3 is indicated by 32; it represents a reference feature in the context of the invention.

The eye tracker 24 transmits the u-v coordinates of the circle center 32 to the control unit 22. This thereupon guides the laser source 14 and the scanner 18 to apply a plurality of test features 34 on the top side 28 of test object 26 through laser irradiation. The test features 34 are small circles, for example, or other geometrical shapes, that stand out optically from the surrounding areas of the top side 28 of test object 26 and are detectable by eye tracker 24. For example, generation of each test feature 34 may require many hundreds or even many thousands of laser pulses to be incident.

The positions at which the test features 34 are applied, are computed by control unit 22 in dependence on the u-v coordinate position of the circle center 32 communicated by eye tracker 24. A preset generation rule determines at which x,y positions the test features 34 are to be applied with reference to circle center 32. An example of a generation rule may specify that four test features $34_1 \ldots 34_4$ are to be applied in a rectangular array about circle center 32, with circle center 32 forming the center of the rectangle. Such a rectangular array of four test features 34 is shown as an example in FIG. 3. The rectangular array there is approximately a square array.

In the example case shown in FIG. 3, it can be perceived that the applied test features 34 in fact are not centric to circle center 32, but rather have a square center 36 that is displaced vis-à-vis circle center 32, defined as the crossing point of two square diagonals. The offset between circle center 32 and square center 26 allows one to conclude there are deviations between the u-v coordinate system of eye tracker 24 and the x-y coordinate system of control unit 22 and of scanner 18. This is because in the case of such deviations, two points with the same numerical coordinate values in the u-v coordinate system and in the x-y coordinate system diverge, as is made clear in FIG. 2 by points $P_1$ and $P_2$. A point in the x-y coordinate system with the same coordinate values as the circle center 32 therefore is not spatially congruent with circle center 32, but rather is displaced from it. Since the test features 34 are generated with reference to this (displaced) point in the x-y coordinate system, they are centric to this point, but not centric to the circle center 32.

For quantitative detection of the deviations between the two coordinate systems the test object 26 provided with test features 34 is again scanned by eye tracker 24, to determine the u-v coordinates of the test features 34 in the u-v coordinate system. From the u,v coordinates of the test features 34, u-v coordinates of the square center 36 are computed in addition. Square center 36 represents a derived feature in the context of the invention, because it is derived from the test features 34.

Based on the u,v positions of the test features 34 thus determined and of the square center 36, information is determined by control unit 22 which characterizes the deviations between the u-v coordinate system and the x-y coordinate system.

Specifically, the u-distance and the v-distance of the square center 36 from circle center 32 permit determination of a displacement vector that characterizes the extent and direction of deviation in position of the origins of the coordinate systems. According to one example, the control unit then computes for at least one pair of test features 34 assigned, initially-corrected u,v positions which are displaced vis-à-vis the test feature 34 concerned by the displacement vector. The initially corrected u,v positions are consequently centered vis-à-vis circle center 32. For example, in FIG. 3, for the test features $34_1$, $34_2$ such initially-corrected u,v positions $34_1'$, $34_2'$ are drawn in, which are shifted vis-à-vis test feature $34_1$ and $34_2$ respectively, to the same degree that the square center 36 is shifted vis-à-vis circle center 32.

The relative twisting of the two coordinate systems can for example be determined by the control unit 22 determining target coordinate positions in the u-v coordinate system for the same pair of test features for which it has determined the initially corrected u,v positions. For this it applies the above-mentioned generation rule for the test features in the u-v coordinate system with reference to the u,v coordinate position of circle center 32. For example, in FIG. 3, the target position thus determined of test feature $34_1$ is drawn in at $34_1^s$ and the target position of test feature $34_2$ is drawn in at $34_2^s$ in the u-v coordinate system.

A twisting of the coordinate systems can easily be determined by comparing the connecting straight line of target coordinate positions $34_1^s$ and $34_2^s$ with the connecting straight line of the initially corrected u,v positions $34_1'$ and $34_2'$. If these two connecting straight lines are parallel, the coordinate systems are not twisted. If they are at an angle to each other, the angle between the connecting straight lines indicates the twisting angle of the coordinate systems.

To determine any scaling differences between the two coordinate systems, control unit 22, with the aid of the determined twisting angle of the coordinate systems from the initially corrected u,v positions of the pair of test features in question, can determine the again-corrected u,v positions, which are corrected by the twisting angle in addition to the degree of shift. As an example, in FIG. 3 the again-corrected u,v positions $34_1''$, $34_2''$ are drawn in for test features $34_1$, $34_2$. The connecting straight lines for these again-corrected u,v positions $34_1''$, $34_2''$ now are parallel to the connecting straight lines of the target coordinate positions $34_1^s$, $34_2^s$.

True, the again-corrected u,v positions $34_1''$, $34_2''$ continue to be non-congruent with the target coordinate positions $34_1^s$, $34_2^s$. This is an indication that the axial scaling of the coordinate systems differs.

By calculating the u-distance of the target coordinate positions $34_1^s$, $34_2^s$ and of the u-distance of the again-corrected u-v positions $34_1''$, $34_2''$ and by comparison (especially quotient formation) of these u-distances, any differing scaling of the u-axis of the u-v coordinate system and of the x-axis of the x-y coordinate system can be recognized and determined quantitatively. The same holds true for any different scaling of the v-axis and of the y-axis which can be recognized and quantitatively determined by calculating the v-distance of the target coordinate positions $34_1^s$, $34_2^s$ and the v-distance of the again-corrected u,v positions $34_1''$, $34_2''$ and by comparison (especially quotient formation) of these v-distances.

Instead of the u-distance or v-distance of the target coordinate positions and the again-corrected u,v positions of a pair of test features, for determining a deviating axial scaling of the coordinate systems, alternatively also the u-distance and/or the v-distance between the target coordinate position of a test feature and the circle center 32 and between the again-corrected u,v position of that same test feature and the circle center 32 can be determined.

It is understood that a rectangular array of test features 34 is purely exemplary and that other polygonal arrays and even a circular array of test features 34 is readily possible.

To make it possible to optically recognize the test features 34, the area of the surface 28 of the test object around the reference pattern 30 can be printed in a color that disappears when irradiated by a laser, thereby allowing another color lying underneath to come into view. For this purpose, test object 26 can comprise a plate-shaped or sheet-shaped substrate, which has a flat printing of an underlying color on its flat sides. On this underlying color, in the area of reference pattern 30, a first different color is printed, which forms reference pattern 30. Outside reference pattern 30, a second other color is printed that can be bleached out by laser irradiation or removed by some other means.

In an alternative embodiment, it is conceivable to print a grid network of fine, closely spaced lines in the area outside reference pattern 30. By local laser irradiation, the grid network can be interrupted at the irradiated locations, for example in using a color for the grid network that can be bleached out by laser action or by the laser generating a crater in the top side 28 of test object 26. The interruption in the grid network thus generated can be recognized by suitable image processing software and used as a test feature.

The device 10 can carry out the above-mentioned method for determining deviations between the u-v and the x-y coordinate systems in fully automatic fashion, as soon as a user inserts test object 26 and gives an appropriate start command. Especially the control unit 22, as part of such an automatic calibration, can determine suitable correction parameters for the coordinate transformation from the u-v coordinate system into the x-y coordinate system, and store them in a memory device which is not depicted in any greater detail.

The invention claimed is:

1. Method for determining deviations between coordinate systems of different technical systems, comprising:
   determining a (u,v) coordinate position of a reference feature of a test object in a coordinate system (u,v) of a first of the technical systems,
   determining a (x,y) coordinate position of at least one test feature from the (u,v) coordinate position of the reference feature, the (x,y) coordinate position expressed in a coordinate system (x,y) of a second of the technical systems, attaching the at least one test feature to the test object at the (x,y) coordinate position using the coordinate system (x,y), determining a (u,v) coordinate position of the at least one test feature or at least one feature derived therefrom in the coordinate system (u,v) of the first technical system, and determining one or more deviations between the coordinate systems of the first and of the second technical according to at least the at least one test feature or at least one feature derived therefrom.

2. Method according to claim 1, wherein a plurality of test features are attached at different places of the test object.

3. Method according to claim 2, the attaching the at least one test feature to the test object further comprising:
attaching at least a part of the test features in a polygonal arrangement around the reference feature on the test object.

4. Method according to claim 3, further comprising:
determining a polygonal center of the test features arranged as a polygon as a derived feature, and
determining, in the coordinate system (u, v) of the first technical system, a deviation between the (u, v) coordinate position of the reference feature and the (u, v) coordinate position of the polygon center.

5. Method according to claim 1, further comprising:
determining the target coordinate position of a test feature in the coordinate system (u, v) of the first technical system in accordance with a coordinate distance preset for this feature from the reference feature in the coordinate system (x, y) of the second technical system.

6. Method according to claim 1, further comprising:
determining the coordinate position of the reference feature and of at least one tested or the derived feature in the first coordinate system (u, v), using a motion tracking device with a camera directed toward the test object, the first technical system comprising the motion tracking device.

7. Method according to claim 1, further comprising:
determining a center of a pattern of the test object as a reference feature.

8. Method according to claim 7, wherein the pattern is a flat pattern, which is optically contrasted with the surrounding area.

9. Method according to claim 7, wherein the pattern possesses a circular or elliptical contour.

10. Method according to claim 1, the attaching the at least one test feature to the test object further comprising:
attaching the at least one test feature to the test object using a laser beam of a laser arrangement that uses the second coordinate system (x, y) to position the laser beam, the second technical system comprising the laser arrangement.

11. Method according to claim 10, the attaching the at least one test feature to the test object further comprising:
treating the test object with the laser beam to change a color of the test object or form a crater on the test object.

12. Method according to claim 1, further comprising:
correcting coordinate date according to at least one determined deviation.

13. Test object for application in a method according to claim 1, wherein the test object possesses an optically emphasized pattern and at least in one area is configured around the pattern, so that through local laser irradiation, optically emphasized test features can be generated.

14. Test object according to claim 13, wherein the pattern is an areal pattern, which appears in a first color, wherein the test object appears in an area around the pattern in a second color.

15. Test object according to claim 13, wherein the test object is configured to have a plate or sheet shape.

16. Device for laser-surgical ophthalmology, comprising:
a laser arrangement that provides and directs a pulsed, focused laser beam at an eye to be treated,
an eye tracker that detects movements of the eye, and
a control unit coupled with the eye tracker, which controls the laser arrangement in response to detected eye movements, wherein the control unit can further:
implement the method according to one of claims 1 to 13, to determine deviations between the first coordinate system (u, v) used by the eye tracker and the second coordinate system (x, y) used by the laser arrangement.

17. Method according to claim 1, where determining one or more deviations between the coordinate systems further comprises:
determining the (x,y) coordinate of the reference feature from the (u,v) coordinate position of the at least one test feature or at least one feature derived therefrom, and
determining a displacement deviation from the (x,y) coordinate of the reference feature and the (u,v) coordinate position of the reference feature.

18. Method according to claim 1, where determining one or more deviations between the coordinate systems further comprises:
determining a displacement deviation according to the (u,v) coordinate position of the reference feature,
correcting the (u,v) coordinate of the reference feature according to the displacement deviation to yield a displacement corrected (u',v') coordinate of the reference feature,
determining a displacement corrected (u',v') coordinate position of a next at least one test feature or at least one feature derived therefrom according to the displacement corrected (u',v') coordinate of the reference feature,
attaching the next at least one test feature to the test object at the displacement corrected (x,y) coordinate position,
determining a target $(u^s,v^s)$ coordinate position of the next at least one test feature or at least one feature derived therefrom, and
determining a twisting deviation from the displacement corrected (u',v') coordinate position of the next at least one test feature or at least one feature derived therefrom and the target $(u^s,v^s)$ coordinate position of the next at least one test feature or at least one feature derived therefrom.

19. Method according to claim 1, where determining one or more deviations between the coordinate systems further comprises:
determining a twisting deviation from a displacement corrected (u',v') coordinate position of a next at least one test feature or at least one feature derived therefrom and a target $(u^s,v^s)$ coordinate position of the next at least one test feature or at least one feature derived therefrom,
correcting the displacement corrected (u',v') coordinate of the at least one test feature or at least one feature derived therefrom according to the twisting deviation to yield a displacement-twisting corrected (u",v") coordinate of the at least one test feature or at least one feature derived therefrom, and determining a scaling deviation from the displacement-twisting corrected $(u'',v'')$ coordinate of the at least one test feature or at least one feature derived therefrom and the target $(u^s,v^s)$ coordinate position of the at least one test feature or at least one feature derived therefrom.

\* \* \* \* \*